United States Patent
Huang et al.

(10) Patent No.: US 9,691,518 B2
(45) Date of Patent: Jun. 27, 2017

(54) MEDICAL CABLE

(71) Applicant: Hitachi Metals, Ltd., Tokyo (JP)

(72) Inventors: Detian Huang, Hitachi (JP); Takanobu Watanabe, Hitachi (JP); Kimika Kudo, Kitaibaraki (JP); Haruyuki Watanabe, Hitachi (JP)

(73) Assignee: HITACHI METALS, LTD., Tokyo (JP)

( * ) Notice: Subject to any disclaimer, the term of this patent is extended or adjusted under 35 U.S.C. 154(b) by 0 days.

(21) Appl. No.: 15/167,185

(22) Filed: May 27, 2016

(65) Prior Publication Data

US 2016/0358689 A1    Dec. 8, 2016

(30) Foreign Application Priority Data

Jun. 3, 2015    (JP) .................................. 2015-112799

(51) Int. Cl.

| H01B 11/06 | (2006.01) |
| H01B 1/22 | (2006.01) |
| A61B 1/00 | (2006.01) |
| A61B 8/00 | (2006.01) |
| H01B 7/04 | (2006.01) |

(52) U.S. Cl.
CPC .......... H01B 1/22 (2013.01); A61B 1/00114 (2013.01); A61B 8/44 (2013.01); H01B 7/04 (2013.01)

(58) Field of Classification Search
CPC ..... H01B 11/06; H01B 11/08; H01B 11/1033; H01B 7/083; H01B 7/0861

USPC ..................... 174/36, 126.4, 117 M
See application file for complete search history.

(56) References Cited

U.S. PATENT DOCUMENTS

| 2,458,243 | A | * | 1/1949 | Biddle | .................... C03C 25/46 |
| | | | | | 174/131 A |
| 7,288,494 | B2 | * | 10/2007 | Iwasaki | ............... H05K 9/0098 |
| | | | | | 139/425 R |
| 7,576,286 | B2 | * | 8/2009 | Chen | ...................... D02G 3/441 |
| | | | | | 174/117 M |
| 8,283,563 | B2 | * | 10/2012 | Harris | ................... D02G 3/441 |
| | | | | | 174/117 M |

FOREIGN PATENT DOCUMENTS

JP    2002367444 A    12/2012

* cited by examiner

*Primary Examiner* — Chau N Nguyen
(74) *Attorney, Agent, or Firm* — Roberts Mlotkowski Safran Cole & Calderon P.C.

(57) ABSTRACT

A medical cable includes a plurality of cables, a braided shield covering a circumference of the plurality of cables together and being formed of tubular braided strands, and a jacket covering a circumference of the braided shield. The braided strands includes a copper foil yarn, which includes a highly stretchable polyethylene terephthalate monofilament yarn having a tensile strength of not lower than 700 MPa and an elongation of not lower than 50 percent and not higher than 100 percent, and a copper strip wound helically at a pitch around a surface of the highly stretchable polyethylene terephthalate monofilament yarn. The copper foil yarn has an entire push and recover ratio of not lower than 80 percent.

5 Claims, 2 Drawing Sheets

MEDICAL CABLE

The present application is based on Japanese patent application No. 2015-112799 filed on Jun. 3, 2015, the entire contents of which are incorporated herein by reference.

BACKGROUND OF THE INVENTION

1. Field of the Invention

This invention relates to a medical cable, which is suitable for medical use.

2. Description of the Related Art

In medical use for ultrasonic diagnosis, endoscopic examination, etc., a medical cable having a plurality of cables, a braided shield, which covers a circumference of the plurality of cables together and which is comprising braided strands each made of a copper wire or a copper alloy wire braided in tubular form, and a jacket covering a circumference of the braided shield has conventionally been being used (See e.g. JP-A-2002-367444).

SUMMARY OF THE INVENTION

In recent years, for the purpose of enhancing the handleability (flexibility) of the medical cable during ultrasonic diagnosis, endoscopic examination, etc. or alleviating a patient discomfort during endoscopic examination as much as possible, softening and diameter reduction of the medical cable have been being promoted.

With the progress of softening and diameter reduction of the medical cable, however, there has arisen the problem that the restoring force of the medical cable (that is a force with which the medical cable returns to its original shape at the time of bending or the like) decreases, thus the medical cable tends to tangle, and cable break tends to occur.

Accordingly, it is an object of the present invention is to provide a medical cable, that is capable of suppressing a decrease in restoring force as well as achieving softening and diameter reduction.

According to an aspect of an embodiment of the invention, a medical cable comprises:

a plurality of cables;

a braided shield covering a circumference of the plurality of cables together, the braided shield comprising tubular braided strands; and a jacket covering a circumference of the braided shield, wherein the braided strands comprises a copper foil yarn, which includes a highly stretchable polyethylene terephthalate monofilament yarn having a tensile strength of not lower than 700 MPa and an elongation of not lower than 50 percent and not higher than 100 percent, and a copper strip wound helically at a pitch around a surface of the highly stretchable polyethylene terephthalate monofilament yarn, the copper foil yarn having an entire push and recover ratio of not lower than 80 percent.

In the above embodiment, the following modifications and changes may be made.

The highly stretchable polyethylene terephthalate monofilament yarn preferably comprises a diameter of not smaller than 50 μm and not larger than 100 μm.

The copper strip preferably comprises a thickness not smaller than 0.1 times and not larger than 0.2 times the diameter of the highly stretchable polyethylene terephthalate monofilament yarn, and a width not smaller than 10 times and not larger than 20 times the thickness of the copper strip.

The pitch preferably comprises a width not smaller than 0.2 times and not larger than 0.3 times a width of the copper strip.

The braided shield preferably comprises a braided density of not lower than 90 percent and not higher than 95 percent, and a braid angle of not smaller than 40 degrees and not larger than 45 degrees.

(Points of the Invention)

The invention allows for providing the medical cable capable of suppressing a decrease in restoring force as well as achieving softening and diameter reduction.

BRIEF DESCRIPTION OF THE DRAWINGS

The preferred embodiments according to the invention will be explained below referring to the drawings, wherein.

DETAILED DESCRIPTION OF THE PREFERRED EMBODIMENTS

Below is described an exemplary embodiment according to the invention, in conjunction with the accompanying drawings.

Figure 1:
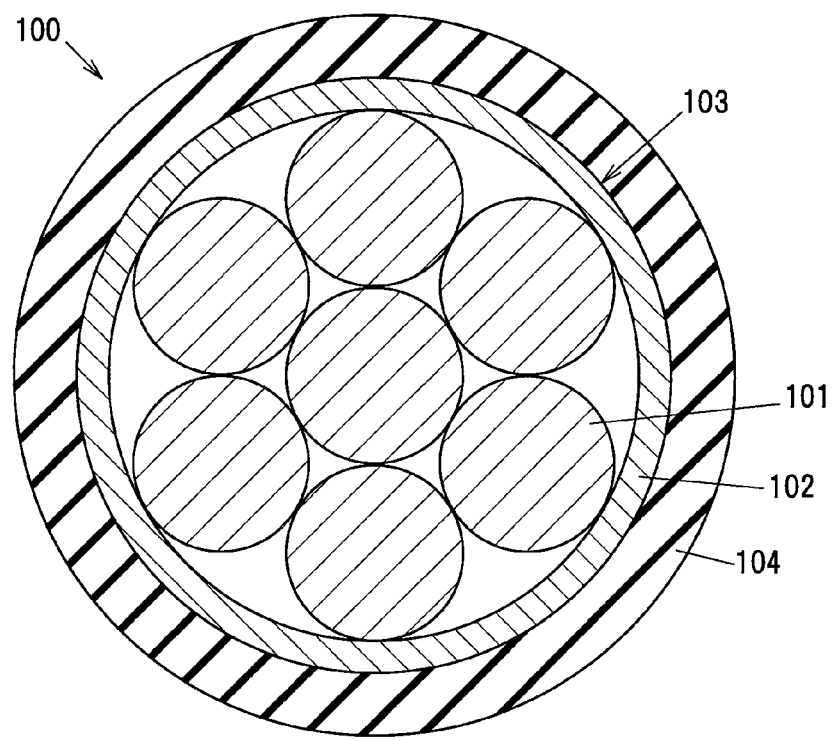
FIG. 1 is a schematic sectional view showing a medical cable according to the present invention.

As shown in FIG. 1, a medical cable 100 in an exemplary embodiment of the present invention includes a plurality of cables 101, a braided shield 103, which covers a circumference of the plurality of cables 101 together and which includes tubular braided strands 102, and a jacket 104, which covers a circumference of the braided shield 103.

As the cables 101, there are listed, e.g., cables as typified by electrical signal transmission cables, optical signal transmission cables and the like, and medical devices as typified by aspiration (suction) tubes, insufflation tubes, infusion tubes, catheters and the like.

Figure 2:
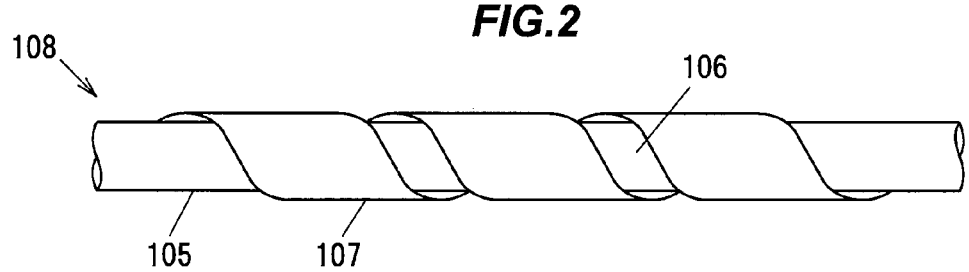
FIG. 2 is a structural schematic diagram showing the copper foil yarn in the medical cable of FIG. 1.

The braided strands 102, as shown in FIG. 2, comprises a copper foil yarn 108, which includes a highly stretchable polyethylene terephthalate monofilament yarn 105 having a tensile strength of not lower than 700 MPa and an elongation of not lower than 50 percent and not higher than 100 percent (i.e. polyethylene terephthalate monofilament yarn having high stretchability), and a copper strip 107 wound helically at a pitch 106 around a surface of the highly stretchable polyethylene terephthalate monofilament yarn 105, and which has an entire push and recover ratio of not lower than 80 percent.

This allows the braided strands 102 to exhibit a stiffness of the same order as that of an annealed copper wire in the medical cable 100, with the copper foil yarn 108 being able to compensate for a decrease in the restoring force of the medical cable 100 at the time of bending of the medical cable 100 due to softening and diameter reduction of the medical cable 100. Therefore, it is possible to suppress the decrease in the restoring force of the medical cable 100 as well as achieve the softening and diameter reduction of the medical cable 100.

Further, in the medical cable 100, the highly stretchable polyethylene terephthalate monofilament yarn 105 is designed to suppress the deformation of the braided shield 103 during bending of the medical cable 100 and allow the braided shield 103 to flexibly follow the bending of the medical cable 100, so that it is possible to maintain the braided shield 103 at a substantially constant braid density and suppress variations in shielding properties during bending of the medical cable 100.

Figure 3:
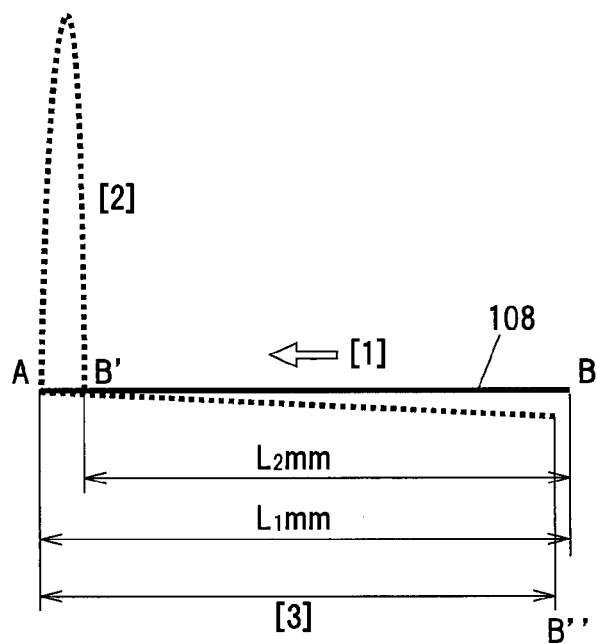
FIG. 3 is a description diagram showing the push and recover ratio of the copper foil yarn.

Note that herein, as shown in FIG. 3, when [1] the copper foil yarn 108 having an initial length of $L_1$ mm represented by the distance between a point A and a point B is installed in a straight line and one end of the copper foil yarn 108 is fixed at the point A, [2] the other end of the copper foil yarn 108 is pushed and moved from the point B toward the point A to a point B' at a moving distance $L_2$ mm ($=L_1 \times 0.9$), followed by releasing the pushing of the other end of the copper foil yarn 108 with the one end of the copper foil yarn 108 being fixed at the point A, and [3] the other end of the copper foil yarn 108 pushes back to a point B" with its elastic force resulting from the releasing of the pushing of the other end of the copper foil yarn 108, the distance from the point A to the point B" is defined as the push and recover length, and the ratio of the push and recover length to the initial length is defined as the push and recover ratio of the copper foil yarn 108.

Further, the braided shield 103 preferably has a braided density (i.e. a percentage of the copper foil yarn 108 per unit area of the braided shield 103) of not lower than 90 percent and not higher than 95 percent. It is because if the braid density of the braided shield 103 is lower than 90 percent, the proportion of electrical conductors per unit volume of the braided strands 102 lowers, therefore no shielding properties required for the medical cable 100 can be ensured. Further, it is because if the braid density of the braided shield 103 is higher than 95 percent, excessive stiffness is imparted to the braided shield 103, leading to loss in the flexibility of the braided shield 103, therefore lowering the handleability of the medical cable 100 during ultrasonic diagnosis, endoscopic examination, etc.

In addition, the braided shield 103 preferably has a braid angle (i.e. a braid angle of the copper foil yarn 108 in the braided shield 103) of not smaller than 40 degrees and not larger than 45 degrees. It is because if the braid angle of the braided shield 103 is smaller than 40 degrees, the shape of the braided shield 103 is more similar to the shape of a tubular shield, therefore leading to difficulty in benefiting from employing of the braided shield 103, i.e., from bending resistance and twisting resistance of the medical cable 100. In addition, it is because if the braid angle of the braided shield 103 is larger than 45 degrees, it is difficult to bring together and draw out the braided shield 103 at the time of termination of the medical cable 100, therefore the terminatability of the medical cable 100 lowers, and excessive stiffness is imparted to the braided shield 103, leading to loss in the flexibility of the braided shield 103, therefore lowering the handleability of the medical cable 100 during ultrasonic diagnosis, endoscopic examination, etc.

The jacket 104 is formed of, e.g., a fluorine resin, such as a tetrafluoroethylene perfluoroalkyl vinyl ether copolymer resin (PFA), a tetrafluoroethylene hexafluoropropylene copolymer resin (FEP), an ethylene tetrafluoroethylene copolymer resin (ETFE) or the like, a silicone resin (SI), a polyurethane resin (PU), or a polyethylene terephthalate resin (PET).

The highly stretchable polyethylene terephthalate monofilament yarn 105 preferably has a diameter of not smaller than 50 μm and not larger than 100 μm, from the point of view of aiming at softening and diameter reduction of the medical cable 100. Because the highly stretchable polyethylene terephthalate monofilament yarn 105, though very thin, as described above, has the tensile strength of not lower than 700 MPa and the elongation of not lower than 50 percent and not higher than 100 percent, adopting the highly stretchable polyethylene terephthalate monofilament yarn 105 allows for imparting the high stiffness and the high push and recover force to the copper foil yarn 108.

The pitch 106 preferably has a width not smaller than 0.2 times and not larger than 0.3 times a width of the copper strip 107. It is because if the width of the pitch 106 is smaller than 0.2 times the width of the copper strip 107, the pitch 106 per unit length of the copper foil yarn 108 decreases, and excessive stiffness is imparted to the copper foil yarn 108, leading to loss in the flexibility of the copper foil yarn 108, therefore lowering the handleability of the medical cable 100 during ultrasonic diagnosis, endoscopic examination, etc. Also, it is because if the width of the pitch 106 is larger than 0.3 times the width of the copper strip 107, the proportion of electrical conductors per unit volume of the braided strands 102 lowers, therefore no shielding properties required for the medical cable 100 can be ensured.

The copper strip 107 preferably has a thickness not smaller than 0.1 times and not larger than 0.2 times the diameter of the highly stretchable polyethylene terephthalate monofilament yarn 105. It is because if the thickness of the copper strip 107 is smaller than 0.1 times the diameter of the highly stretchable polyethylene terephthalate monofilament yarn 105, the proportion of electrical conductors per unit volume of the braided strands 102 lowers, therefore no shielding properties required for the medical cable 100 can be ensured. Further, it is because if the thickness of the copper strip 107 is larger than 0.2 times the diameter of the highly stretchable polyethylene terephthalate monofilament yarn 105, the stiffness of the copper strip 107 in the braided strands 102 is greater than the stiffness of the highly stretchable polyethylene terephthalate monofilament yarn 105, therefore leading to failure to benefit from employing of the highly stretchable polyethylene terephthalate monofilament yarn 105 and suppress the decrease in the restoring force of the medical cable 100, and the excessive stiffness is imparted to the copper foil yarn 108, leading to loss in the flexibility of the copper foil yarn 108, therefore lowering the handleability of the medical cable 100 during ultrasonic diagnosis, endoscopic examination, etc.

Furthermore, the copper strip 107 preferably has a width not smaller than 10 times and not larger than 20 times the thickness of the copper strip 107. It is because if the width of the copper strip 107 is smaller than 10 times the thickness of the copper strip 107, the proportion of electrical conductors per unit volume of the braided strands 102 lowers, therefore no shielding properties required for the medical cable 100 can be ensured. Further, it is because if the width of the copper strip 107 is larger than 20 times the thickness of the copper strip 107, the pitch 106 per unit length of the copper foil yarn 108 decreases, and excessive stiffness is imparted to the copper foil yarn 108, leading to loss in the flexibility of the copper foil yarn 108, therefore lowering the handleability of the medical cable 100 during ultrasonic diagnosis, endoscopic examination, etc.

As described above, the present invention allows for providing the medical cable 100 capable of suppressing a decrease in the restoring force as well as achieving softening and diameter reduction.

EXAMPLES

Below are described examples of the present invention with reference to the accompanying drawings.

Here, evaluation of bending resistance was conducted according to the following procedure.

In the present examples, as the cables, coaxial cables were used including a central conductor formed of seven stranded copper alloy strands each having a diameter of 20 μm, an electrical insulator covering a circumference of the central conductor and formed of a tetrafluoroethylene perfluoroalkyl vinyl ether copolymer resin, an outer conductor with a tin plated copper alloy strand having a tensile strength of 700 MPa and a diameter of 25 μm formed in such a manner as to be wound helically around the electrical insulator, and a covering covering a circumference of the outer conductor and formed of a tetrafluoroethylene perfluoroalkyl vinyl ether copolymer resin, and the cables had an outer diameter of 270 μm.

Further, in the present examples, as the braided shield, braided sleeves were used that were made of a copper foil yarn including a highly stretchable polyethylene terephthalate monofilament yarn having a tensile strength of 800 MPa, an elongation of 80 percent, and a diameter of 80 μm and a copper strip wound helically at a pitch around a surface of the highly stretchable polyethylene terephthalate monofilament yarn, and made of a 12 μm thick and 180 μm wide flat copper alloy strip formed by rolling a round copper alloy wire (99.7 mass % Cu-0.3 mass % Sn) having a tensile strength of 800 MPa and a diameter of 50 μm, and the copper foil yarns had an entire push and recover ratio of 75 percent, 80 percent, or 85 percent and an outer diameter of 104 μm. The push and recover ratio of the copper foil yarns is adjusted by varying the pitch of the copper strip.

Figure 4:
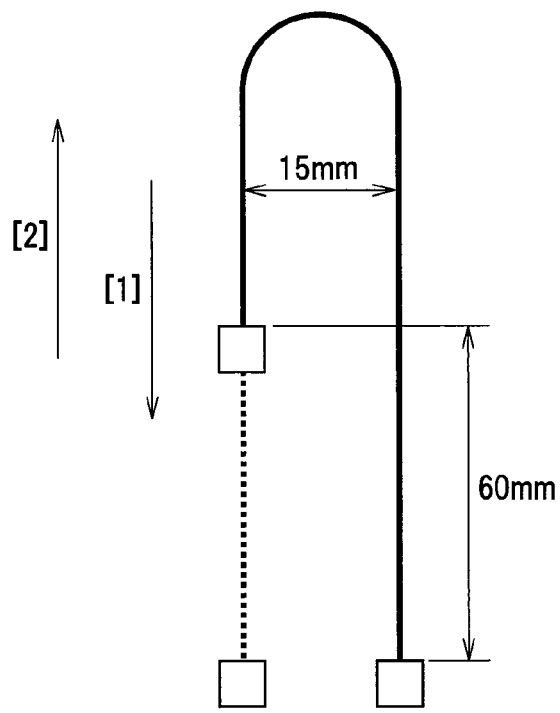
FIG. 4 is an explanatory diagram showing the evaluation procedure for bending resistance.

In evaluating the bending resistance, the braided sleeves were applied to a circumference of the 12 coaxial cables to produce samples having an outer diameter of about 1.5 mm, and those samples were wired in an about 2.0 mm high wiring space. Thereafter, as shown in FIG. 4, one end of a sample 400 was fixed while the other end thereof was bent in such a U shape that the slide inner width was 15 mm while the stroke length was 60 mm, and the other end of the sample 400 was U-shape slid cyclically in alternating [1] and [2] arrow directions.

At this point, testing was conducted in such a manner that the number of U-shape slidings performed per unit time was 30 cycles/minute, and that a voltage was continuously applied to the coaxial cables, to measure a time at which that voltage value decreased by 20 percent from when the testing was started, and at which cable break was determined to occur, and examine how many cycles the sample 400 lasted. The results thereof are shown in Table 1 below.

TABLE 1

|  | Comparative example 1 | Example 1 | Example 2 |
|---|---|---|---|
| Copper foil yarn push and recover ratio | 75% | 80% | 85% |
| Bending resistance evaluation | Fail | Pass | Pass |

Herein, a "Pass" was given for not lower than 200 thousand cycles, or a "Fail" was given for lower than 200 thousand cycles.

As can be seen from Table 1, Example 1 and Example 2, which were not lower than 80 percent in the copper foil yarn push and recover ratio, were able to withstand the U-shape slidings of not lower than 200 thousand cycles, whereas Comparative example 1, which had the copper foil yarn push and recover ratio of 75 percent, was unable to withstand the U-shape slidings of not lower than 200 thousand cycles.

From the above results, it is found that it is necessary to employ the copper foil yarn having a push and recover ratio of not lower than 80 percent.

Although the invention has been described with respect to the specific embodiments for complete and clear disclosure, the appended claims are not to be thus limited but are to be construed as embodying all modifications and alternative constructions that may occur to one skilled in the art which fairly fall within the basic teaching herein set forth.

What is claimed is:

1. A medical cable, comprising:
a plurality of cables;
a braided shield covering a circumference of the plurality of cables together, the braided shield comprising tubular braided strands; and
a jacket covering a circumference of the braided shield,
wherein the braided strands comprises a copper foil yarn, which includes a highly stretchable polyethylene terephthalate monofilament yarn having a tensile strength of not lower than 700 MPa and an elongation of not lower than 50 percent and not higher than 100 percent, and a copper strip wound helically at a pitch around a surface of the highly stretchable polyethylene terephthalate monofilament yarn, the copper foil yarn having an entire push and recover ratio of not lower than 80 percent.

2. The medical cable according to claim 1, wherein the highly stretchable polyethylene terephthalate monofilament yarn comprises a diameter of not smaller than 50 μm and not larger than 100 μm.

3. The medical cable according to claim 1, wherein the copper strip comprises a thickness not smaller than 0.1 times and not larger than 0.2 times the diameter of the highly stretchable polyethylene terephthalate monofilament yarn, and a width not smaller than 10 times and not larger than 20 times the thickness of the copper strip.

4. The medical cable according to claim 1, wherein the pitch comprises a width not smaller than 0.2 times and not larger than 0.3 times a width of the copper strip.

5. The medical cable according to claim 1, wherein the braided shield comprises a braided density of not lower than 90 percent and not higher than 95 percent, and a braid angle of not smaller than 40 degrees and not larger than 45 degrees.

* * * * *